US006573049B1

(12) United States Patent
Schappert

(10) Patent No.: US 6,573,049 B1
(45) Date of Patent: Jun. 3, 2003

(54) GENOTYPING OF THE PARAOXONASE 1 GENE FOR PROGNOSING, DIAGNOSING, AND TREATING A DISEASE

(75) Inventor: Keith Schappert, Montreal (CA)

(73) Assignee: Nuvelo, Inc., Cambridge, MA (US)

( * ) Notice: Subject to any disclaimer, the term of this patent is extended or adjusted under 35 U.S.C. 154(b) by 0 days.

(21) Appl. No.: 09/616,506

(22) Filed: Jul. 14, 2000

Related U.S. Application Data

(60) Provisional application No. 60/145,602, filed on Jul. 26, 1999.

(51) Int. Cl.[7] .......................... C07H 21/04; C12Q 1/68
(52) U.S. Cl. .......................................... 435/6; 536/23.1
(58) Field of Search ............................ 435/6; 536/23.1

(56) References Cited

U.S. PATENT DOCUMENTS

| | | | | |
|---|---|---|---|---|
| 5,547,835 A | 8/1996 | Köster | ........................... | 435/6 |
| 5,869,242 A | 2/1999 | Kamb | ........................... | 435/6 |
| 5,935,781 A | 8/1999 | Poirier | .......................... | 435/6 |
| 6,022,683 A | 2/2000 | Poirier | .......................... | 435/4 |
| 6,242,186 B1 | 6/2001 | Salonen | ......................... | 435/6 |
| 6,251,587 B1 | 6/2001 | Sévigny et al. | ................ | 435/6 |

FOREIGN PATENT DOCUMENTS

WO WO 00/30425 6/2000

OTHER PUBLICATIONS

Sanghera et al. "The codon 55 polymorhpism in the paraoxonase 1 gene is not associated with the risk of coronary heart disease in Asian Indians and Chinese" Artherosclerosis, vol. 136, No. 2, p. 217–223, Feb. 1998.*

Dessi et al. "Influence of the human paraoxonase polymorphism (PON1 192) on the carotid–wall thickenin in a healthy population" Coronary Artery Disease, vol. 10, No. 8, p. 595–599, Dec. 1999.*

Cascorbi et al. "Mutations in the human paraoxonase 1 gnee: frequencies, allelic linkages and association with coronary artery disease" vol. 9, No. 6, p. 755–761, Dec. 1999.*

Garin et al. "Paraoxonase polymorphism Met–Leu54 is associated with modified serum concentration of the enzyme" J. of Clinical Investigation, vol. 99, No. 1, p. 62–66, Jan. 1997.*

Schmidt et al. "Paraoxonase PON1 polymorphism Leu-Met54 is associated with carotid atherosclerosis" Stroke vol. 29, No. 10, p. 2043–2048, Oct. 1998.*

Zama et al. "A 192Arg variant of the HUMPONA gnee polymorphsi is associated with an increased risk for coronary artery disease in Japanese" Arteriosclerosis, Thrombosis, and Vascular Biology, vol. 17, No. 12, p. 3565–3569, Dec. 1997.*

Mackness et al. "Serum paraoxonase (PON1) 55 and 192 polymorphism and paraoxonase activity and concentration in non–insulin dependent diabetes mellitus" Artherosclerosis, Vol. 139, No. 2, p. 341–349, Aug. 1998.*

Malin et al. "The Met54Leu polymorphism of PON enzyme gne is not a genetic risk facotr for non–insulin–dependent diabetes mellitus in Flnns" Clinical Genetics, Vol. 54, No. 3, p. 254–255, 1998.*

Sodeyama et al. "No association of paraoxonase gnee polymorphism with atherosclerosis or Alzheimer's disease" Neurology, vol. 53, No. 5, p. 1146–1148, Sep. 1999.*

Wang et al. "No association between PON1 gnee polymorphism and susceptibility to Parkinson's Disease in a Chinese Population" Movement Disorders, Vol. 15, No. 6, p. 1265–1266, 2000.*

Kondo et al., "Genetic polymorphism of paraoxonase 1 (PON1) and susceptibility to Parkinson's Disease," Brain Research 806(2):271–73 (1998).

Del Colle et al., "Serum paraoxonase activity is an independent risk factor for stroke: Comparison with homocystein, fibrinogen and lipoprotein parameters," Journal of Neurological Sciences 150:S84 (1997).

Mackness et al., "Paraoxonase and Coronary Heart Disease," Current Opinion in Lipidology 9(4):319–324 (1998).

Laplaud et al., "Paraoxonase as a risk marker for cardiovascular disease: Facts and Hypotheses," Clinical Chemistry and Laboratory Medicine 36(7):431–441 (1998).

Brindle N. et al., "Analysis of the butyrylcholinesterase gene and nearby chromosome 3 markers in Alzheimer disease," Hum. Mol. Genet. 7:933–935 (1998).

Cummings et al., "Alzheimer's disease Etiologies, pathophysiology, cognitive reserve, and treatment opportunities," Neurology (1 Suppl 1):S2–S17 (1998).

Dessi et al., "Influence of the human paraoxonase polymorphism (PON1 192) on the carotid–wall thickening in a healthy population," Coronary Artery Disease 10:595–599 (1999).

Gustincich S. et al., "A Fast Method for High–Quality Genomic DNA Extraction from Whole Human Blood," Biofeedback: Short Technical Reports: Biotechniques 11:298–300 (1998).

Lehmann et al., "Synergy between the genes for butyrylcholinesterase K variant and apolipoprotein E4 in late–onset confirmed Alzheimer's disease," Hum. Mol. Genet. 6:1933–1936 (1997).

Mackness et al., "Human Serum Paraoxonase," Gen. Pharmac. 31:329–336 (1998).

Richard et al., "*APOE* genotyping and response to drug treatment in Alzheimer's disease," Lancet 349:539 (1997).

Singleton et al., "No association between the K variant of the butyrylcholinesterase gene and pathologically confirmed Alzheimer's disease," Hum. Mol. Genet. 7:937–939 (1998).

* cited by examiner

*Primary Examiner*—W. Gary Jones
*Assistant Examiner*—Jeanine Goldberg
(74) *Attorney, Agent, or Firm*—Clark & Elbing LLP; Kristina Bieker-Brady

(57) ABSTRACT

The invention provides methods for identifying or stratifying subjects having Alzheimer's disease or at risk for Alzheimer's disease by determining the genotype at nucleotide 172 of the PON1 allele of the subject.

7 Claims, 4 Drawing Sheets

```
1    cccccgacca tggcgaagct gattgcgctc accctcttgg ggatgggact ggcactcttc
61   aggaaccacc agtcttctta ccaaacacga cttaatgctc tccgagaggt acaacccgta
121  gaacttccta actgtaattt agttaaagga atcgaaactg gctctgaaga cttggagata
181  ctgcctaatg gactggcttt cattagctct ggattaaagt atcctggaat aaagagcttc
241  aaccccaaca gtcctggaaa aatacttctg atggacctga atgaagaaga tccaacagtg
301  ttggaattgg ggatcactgg aagtaaattt gatgtatctt catttaaccc tcatgggatt
361  agcacattca cagatgaaga taatgccatg tacctcctgg tggtgaacca tccagatgcc
421  aagtccacag tggagttgtt taaatttcaa gaagaagaaa aatcgctttt gcatctaaaa
481  accatcagac ataaacttct gcctaatttg aatgatattg ttgctgtggg acctgagcac
541  ttttatggca caaatgatca ctattttctt gacccctact tacaatcctg ggagatgtat
601  ttgggtttag cgtggtcgta tgttgtctac tatagtccaa gtgaagttcg agtggtggca
661  gaaggatttg attttgctaa tggaatcaac atttcacccg atggcaagta tgtctatata
721  gctgagttgc tggctcataa gattcatgtg tatgaaaagc atgctaattg gactttaact
781  ccattgaagt cccttgactt taataccctc gtggataaca tatctgtgga tcctgagaca
841  ggagaccttt gggttggatg ccatcccaat ggcatgaaaa tcttcttcta tgactcagag
901  aatcctcctg catcagaggt gcttcgaatc cagaacattc taacagaaga acctaaagtg
961  acacaggttt atgcagaaaa tggcacagtg ttgcaaggca gtacagttgc ctctgtgtac
1021 aaagggaaac tgctgattgg cacagtgttt cacaaagctc tttactgtga gctctaacag
1081 accgatttgc acccatgcca tagaaactga ggccattatt tcaaccgctt gccatattcc
1141 gaggacccag tgttcttagc tgaacaatga atgctgaccc taaatgtgga catcatgaag
1201 catcaaagca ctgtttaact gggagtgata tgatgtgtag ggcttttttt tgagaataca
1261 ctatcaaatc agtcttggaa tacttgaaaa cctcatttac cataaaaatc cttctcacta
1321 aaatggataa atcagttaaa aaaaaa
```

Fig. 1

```
1    cccccgacca tggcgaagct gattgcgctc accctcttgg ggatgggact ggcactcttc
61   aggaaccacc agtcttctta ccaaacacga cttaatgctc tccgagaggt acaacccgta
121  gaacttccta actgtaattt agttaaagga atcgaaactg gctctgaaga cAtggagata
181  ctgcctaatg gactggcttt cattagctct ggattaaagt atcctggaat aaagagcttc
241  aaccccaaca gtcctggaaa aatacttctg atggacctga atgaagaaga tccaacagtg
301  ttggaattgg ggatcactgg aagtaaattt gatgtatctt catttaaccc tcatgggatt
361  agcacattca cagatgaaga taatgccatg tacctcctgg tggtgaacca tccagatgcc
421  aagtccacag tggagttgtt taaatttcaa gaagaagaaa aatcgctttt gcatctaaaa
481  accatcagac ataaacttct gcctaatttg aatgatattg ttgctgtggg acctgagcac
541  ttttatggca caaatgatca ctattttctt gacccctact tacaatcctg ggagatgtat
601  ttgggtttag cgtggtcgta tgttgtctac tatagtccaa gtgaagttcg agtggtggca
661  gaaggatttg attttgctaa tggaatcaac atttcacccg atggcaagta tgtctatata
721  gctgagttgc tggctcataa gattcatgtg tatgaaaagc atgctaattg gactttaact
781  ccattgaagt cccttgactt taataccctc gtggataaca tatctgtgga tcctgagaca
841  ggagaccttt gggttggatg ccatcccaat ggcatgaaaa tcttcttcta tgactcagag
901  aatcctcctg catcagaggt gcttcgaatc cagaacattc taacagaaga acctaaagtg
961  acacaggttt atgcagaaaa tggcacagtg ttgcaaggca gtacagttgc ctctgtgtac
1021 aaagggaaac tgctgattgg cacagtgttt cacaaagctc tttactgtga gctctaacag
1081 accgatttgc acccatgcca tagaaactga ggccattatt tcaaccgctt gccatattcc
1141 gaggacccag tgttcttagc tgaacaatga atgctgaccc taaatgtgga catcatgaag
1201 catcaaagca ctgtttaact gggagtgata tgatgtgtag ggcttttttt tgagaataca
1261 ctatcaaatc agtcttggaa tacttgaaaa cctcatttac cataaaaatc cttctcacta
1321 aaatggataa atcagttaaa aaaaaa
```

Fig. 2

MAKLIALTLLGMGLALFRNHQSSYQTRLNALREVQPVELPNCNL
VKGIETGSEDLEILPNGLAFISSGLKYPGIKSFNPNSPGKILLMDLNEEDPTVLELGI
TGSKFDVSSFNPHGISTFTDEDNAMYLLVVNHPDAKSTVELFKFQEEEKSLLHLKTIR
HKLLPNLNDIVAVGPEHFYGTNDHTFLDPYLQSWEMYLGLAWSYVVYYSPSEVRVVAE
GFDFANGINISPDGKYVYIAELLAHKIHVYEKHANWTLTPLKSLDFNTLVDNISVDPE
TGDLWVGCHPNGMKIFFYDSENPPASEVLRIQNILTEEPKVTQVYAENGTVLQGSTVA
SVYKGKLLIGTVFHKALYCEL

Fig. 3

MAKLIALTLLGMGLALFRNHQSSYQTRLNALREVQPVELPNCNL

VKGIETGSEDMEILPNGLAFISSGLKYPGIKSFNPNSPGKILLMDLNEEDPTVLELGI

TGSKFDVSSFNPHGISTFTDEDNAMYLLVVNHPDAKSTVELFKFQEEEKSLLHLKTIR

HKLLPNLNDIVAVGPEHFYGTNDHTFLDPYLQSWEMYLGLAWSYVVYYSPSEVRVVAE

GFDFANGINISPDGKYVYIAELLAHKIHVYEKHANWTLTPLKSLDFNTLVDNISVDPE

TGDLWVGCHPNGMKIFFYDSENPPASEVLRIQNILTEEPKVTQVYAENGTVLQGSTVA

SVYKGKLLIGTVFHKALYCEL

Fig. 4

GENOTYPING OF THE PARAOXONASE 1 GENE FOR PROGNOSING, DIAGNOSING, AND TREATING A DISEASE

CROSS REFERENCE TO RELATED APPLICATIONS

This application claims benefit of provisional application Ser. No. 60/145,602, filed Jul. 26, 1999.

FIELD OF THE INVENTION

In general, the present invention relates to methods for diagnosing or treating a disease, as well as for identifying a subject for participation in a clinical trial, and identifying a subject at risk for a disease.

BACKGROUND OF THE INVENTION

Many diseases are difficult to diagnose because the appropriate diagnostic tools have not yet been identified. The ability to predict that an a symptomatic subject is at risk for developing a disease is even more difficult. A method that would provide a better means by which a disease could be diagnosed, or the risk of developing a disease could be assessed, would be beneficial. The result of having better diagnostic or risk assessment tools would be the more timely administration of appropriate therapies. In addition, not all patients with the same disease respond with equal efficacy to the same therapy. The genotype of a patient may affect the pharmacological efficiency among patients having the same disease. If the genotype of a diseased patient is known, optimal therapies can be determined and administered for the patient, resulting in a faster recovery from the disease.

SUMMARY OF THE INVENTION

The present invention provides methods for diagnosing or treating a disease, as well as for identifying a subject for participation in a clinical trial, and for identifying a subject at risk for a disease. The methods of the invention involve genotyping or phenotyping subjects for the presence of a variant PON1 allele. The information obtained from the determination of the PON1 allele status can be used to diagnose the subject as having a disease, or to identify the subject as being at risk for a disease, or to determine the appropriate therapy for the subject. PON1 allele status determination can also be helpful in designing and assessing the results of a clinical trial aimed at developing a therapy for the treatment of a disease. In a related aspect, the invention features a treatment protocol that provides a prediction of patient outcome.

The human PON1 gene, as reviewed by Mackness et al. (Gen. Pharmac. 31:329–336, 1998), encodes a serum paraoxonase protein. The protein is a 45-kDa glycoprotein that is associated with high density lipoprotein. The protein functions by hydrolyzing organophosphate insecticides and nerve gases, and is responsible for determining the selective toxicity of these compounds in mammals.

Historically, the amino acid residues of the paraoxonase protein may be numbered in two different ways. The amino acids of paraoxonase may be numbered with methionine (beginning at base pair 10) or with alanine (beginning at base pair 13; as used herein) as the first amino acid (see FIG. 1; SEQ ID NO:1). A variant PON1 allele may occur, for example, at amino acid position 54, as used herein, or 55, depending on which numbering system is used. For this reason, the mutation Met54Leu is equal to the mutation Met55Leu. For clarity, this application utilizes the numbering system beginning with alanine as the first amino acid, and therefore refers to PON1 alleles at amino acid positions 54 and 191.

Accordingly, in one aspect, the present invention features a method for identifying a subject at risk for a disease. The method includes genotyping or phenotyping the PON1 locus of a subject, and determining the presence of a variant PON1 allele or isoform. The presence of such a variant allele or isoform indicates an increased risk for the disease.

In a second aspect, the present invention features a method for diagnosing a subject with a disease. The method includes genotyping or phenotyping the PON1 locus of a subject, and determining the presence of a variant PON1 allele or isoform. The presence of such a variant allele or isoform indicates an increased risk for the disease.

In a third aspect, the present invention features a method for identifying a subject for participation in a clinical trial of a therapy for the treatment of a disease. The method includes genotyping or phenotyping the PON1 locus of a subject, and determining the presence of a variant PON1 allele or isoform, where the presence of a variant PON1 allele or isoform places the subject into a subgroup for a clinical trial of a drug.

In a fourth aspect, the present invention features a method of treating a subject with a disease. The method includes genotyping or phenotyping the PON1 locus of a subject, determining the presence of a variant PON1 allele or isoform, and determining the preferred therapy for the treatment of the disease.

In preferred embodiments of all of the above aspects of the invention, the disease may be a neurological disease. The neurological disease can be Alzheimer's disease (AD), or a non-Alzheimer's disease neurological disease (non-AD). In a preferred embodiment, the neurological disease is Alzheimer's disease, neurofibromatosis, Huntington's disease, depression, amyotrophic lateral sclerosis, multiple sclerosis, stroke, Parkinson's disease, or multi-infarct dementia. In further embodiments of the above aspects of the invention, the variant PON1 allele or isoform contains a deletion, insertion, or missense mutation. In another preferred embodiment, the PON1 allele status is heterozygous or homozygous for the PON1 Met54Leu allele.

In preferred embodiments of the invention, the therapy can be a cholinomimetic therapy (e.g. tacrine) or a non-cholinomimetic therapy (e.g., a vasopressinergic therapy). In another preferred embodiment, the therapy can be probucol, a monoamine oxidase inhibitor, a muscarinic agonist, a neurotrophic factor, a noradrenergic factor, an antioxidant, an anti-inflammatory agent, corticotrophin-releasing hormone (CRH), somatostatin, substance P, neuropeptide Y, and thyrotrophin-releasing hormone (TRH).

In a particular application of the invention, all of the above aspects feature a determination of the PON1 allele status of the subject, where a determination of the PON1 allele status, e.g., of the Met54Leu variant, as being heterozygous or homozygous, is predictive of the patient having a poor response to a therapy for a neurological disease (e.g., Alzheimer's disease).

The invention also provides a method for treating a patient at risk for a disease by a) identifying a patient with a risk, b) determining the PON1 allele status of the patient, and c) converting the data obtained in step b) into a treatment protocol that includes a comparison of the PON1 allele status with the allele frequency of a control population. This comparison allows for a statistical calculation of the patient's risk for having a particular disease. In preferred embodiments, the method provides a treatment protocol that predicts a patient being heterozygous or homozygous for the Met54Leu allele to respond poorly to a cholinomimetic (e.g., tacrine) or specific non-cholinomimetic (e.g., vasopressinergics) therapy for a neurological disease, and a patient who is wild type homozygous, to respond favorably to the therapy.

The invention also provides treating a patient at risk for, or diagnosed with, a disease using the above method, and conducting an additional step c) which involves determining the apolipoprotein E allele (e.g., apoE4) or butyrylcholinesterase allele (e.g., BCHE-K) load status of the patient. This method further involves converting the data obtained in steps b) and c) into a treatment protocol that includes a comparison of the allele status of these steps with the allele frequency of a control population. This affords a statistical calculation of the patient's risk for having a disease, for example, a neurological disease. In a preferred embodiment, the method is useful for treating a neurological disease such as Alzheimer's disease, neurofibromatosis, Huntington's disease, depression, amyotrophic lateral sclerosis, multiple sclerosis, stroke, Parkinson's disease, or multi-infarct dementia. In addition, in related embodiments, the methods provide a treatment protocol that predicts a patient to be at high risk for a neurological disease and responding poorly to a cholinomimetic or particular non-cholinomimetic therapy (e.g., vasopressinergics) if the patient is determined to have all or any combination of a PON1 Met54Leu allele, an apoE4 allele, and a BCHE-K allele. Such patients are preferably given an alternative therapy.

The treatment protocol can include a therapy plan for a patient using genetic and diagnostic data, including the patient's neurological diagnosis and PON1, BCHE, and ApoE genotypes. The protocol enhances therapeutic options and clarifies prognoses. The treatment protocol may include an indication of whether or not the patient is likely to respond positively to a cholinomimetic or non-cholinomimetic therapy. The treatment protocol may also include an indication of appropriate drug dose, recovery time, age of disease onset, rehabilitation time, symptomology of attacks, and risk for future disease. A treatment protocol, including any of the above aspects, may also be formulated for a symptomatic and healthy subjects in order to forecast future disease risks and determine what preventive therapies should be considered or invoked in order to decrease these disease risks. The treatment protocol may include the use of a computer software program to analyze patient data.

Genotype determinations can be compiled to predict either prognosis, drug efficacy, or suitability of a patient for participating in clinical trials of a neurological disease therapeutic. For example, the genotype may be compiled with other patient parameters such as age, sex, disease diagnosis, and known allelic frequency of a representative control population. A determination of the statistical probability of the patient having a particular disease risk, drug response, or patient outcome may be assessed from such genotype determinations. Patient outcome, i.e. a prediction of a patient's likely health status, may include a prediction of the patient's response to therapy, rehabilitation time, recovery time, cure rate, rate of disease progression, predisposition for future disease, or risk of having relapse.

The invention also provides a method for improving the efficacy of a therapy for the treatment of diseases. The method includes the step of comparing the relative efficacy of the therapy in patients having different PON1 alleles. Preferably, administration of the drug is preferentially provided to those patients with a PON1 allele type associated with increased efficacy. In a preferred embodiment, the alleles of PON1 used are wild type PON1 and PON1 associated with reduced biological activity. Most preferably the allele associated with reduced biological activity is PON1 Met54Leu.

By "disease" is meant a condition of a living animal that impairs the normal performance or function of the animal.

As used herein, by "genotyping" is meant determination of the type and number of alleles present in a subject, whether determined by nucleic acid sequencing, PCR or RT-PCR amplification, examination of PON1 protein, or by other methods available to those skilled in the art. A specific gene can be genotyped to determine if the gene is a wild-type or variant allele.

By "phenotyping" is meant to determine the detectable outward manifestations of a genotype. For example, the detection of a polypeptide using an epitope-specific antibody is one method of phenotyping.

By "PON1 gene" is meant a gene encoding the paraoxonase polypeptide. In one embodiment, the PON1 gene is human.

By "paraoxonase protein" or "paraoxonase polypeptide" is meant a polypeptide or fragment thereof, encoded by the PON1 gene. In one embodiment, the paraoxonase protein or polypeptide is human.

By "PON1 allele status" is meant a determination of the relative ratio of wild type paraoxonase alleles compared to an allelic variant that may encode a paraoxonase gene product of reduced catalytic activity. This may be accomplished by nucleic acid sequencing, RT-PCR, PCR, examination of the paraoxonase protein, a determination of the paraoxonase enzyme activity, or by other methods available to those skilled in the art.

By "wild-type" is meant any allele, or polypeptide encoded by such an allele, that is present in that part of the population considered free of the particular disease for which the variant allele is being assessed for association with prognosis, diagnosis, or therapeutic efficacy.

By "variant PON1 allele" is meant any sequence mutation of the paraoxonase (PON1) gene that differs from the predominant wild-type allelic sequence (e.g., a variant PON1 allele that changes amino acid residue 54 from leucine to methionine) and which may result in abnormal paraoxonase activity (including protein levels). A variant PON1 allele not specifically described to be associated with a disease herein can be tested for association using the techniques provided herein and those known in the art.

By "paraoxonase activity" is meant the function of the paraoxonase protein. Function includes, but is not limited to, protein level, degree of enzymatic function, and interactions of paraoxonase with other molecules, including, but not limited to polypeptides and nucleic acids.

By "treating" is meant the medical management of a subject, e.g., a human patient, with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder;

preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. "Treating" also includes symptomatic treatment, that is, treatment directed toward constitutional symptoms of the associated disease, pathological condition, or disorder. Thus "treating" includes submitting or subjecting a subject to a compound which will promote the elimination or reduction of a disease or symptoms of a disease, or which will slow the progression of said disease. For example, a subject may be treated with, synthesized organic molecules, naturally occurring organic molecules, peptides, polypeptides, nucleic acid molecules, and components thereof "Treating" also includes the act of not giving a subject a contra-indicated therapeutic.

As used herein, by "deletion mutation" is meant a mutation in a gene resulting from the absence of at least one nucleotide, when compared to the wild- type nucleotide sequence. A polypeptide encoded by a deletion mutation gene may contain an altered amino acid sequence. The polypeptide may be shortened, lengthened, or contain different amino acids as compared to the polypeptide encoded by the wild-type gene.

By "insertion mutation" is meant a mutation in a gene resulting from the insertion of at least one nucleotide, when compared to the wild-type nucleotide sequence. A polypeptide encoded by an insertion mutation gene may contain an altered amino acid sequence. The polypeptide may be shortened, lengthened, or contain different amino acids as compared to the polypeptide encoded by the wild-type gene.

By "missense mutation" is meant a mutation in a gene resulting from the substitution of at least one nucleotide in the sequence for another, when compared to the wild-type nucleotide sequence. A polypeptide encoded by a missense mutation gene may contain an altered amino acid sequence. The polypeptide may be shortened, lengthened, or contain different amino acids as compared to the polypeptide encoded by the wild-type gene.

By "homozygous for the PON1 Met54Leu allele" is meant that both copies of the PON1 allele in a cell are identical, and encode a methionine at amino acid position 54 of the paraoxonase polypeptide.

By "heterozygous for the PON1 Met54Leu allele" is meant that the two copies of the PON 1 allele in a cell are not identical. For example a cell which is heterozygous for the PON1 Met54Leu allele contains one allele which codes for a methionine at amino acid position 54 of the paraoxonase polypeptide, while the other allele codes for a leucine at the same amino acid position.

By "neurological disease" is meant a disease which involves the neuronal cells of the nervous system. Specifically included are: prior diseases (e.g., Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, tyrosinemia, and fragile X syndrome); pathologies of the mature brain (e.g., neurofibromatosis, Huntington's disease, depression, amyotrophic lateral sclerosis, multiple sclerosis); conditions that strike in adulthood (e.g., Alzheimer's disease, Creutzfeldt-Jakob disease, Lewy body disease, Parkinson's disease, Pick's disease); and other pathologies of the brain (e.g., brain mishaps, brain injury, coma, infections by various agents, dietary deficiencies, stroke, multiple infarct dementia, and cardiovascular accidents).

By "Alzheimer's disease" or "AD" is meant a pathology characterized by an early and extensive loss of entorhinal cortex neurons. Alzheimer's disease subjects may be identified by progressive and degenerative effects on the brain which are not attributable to other causes. A diagnosis of Alzheimer's disease is made using clinical-neuropathological correlations known in the art (see e.g., *Arch. Neurology* 51:888–896, 1994). Post-mortem, the disease may be diagnosed by the presence of amyloid plaques and fibrils.

By "non-AD neurological disease" is meant a disease other than Alzheimer's disease, which involves the neuronal cells of the nervous system. Specifically included are: prior diseases (e.g, Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, tyrosinemia, and fragile X syndrome); pathologies of the mature brain (e.g., neurofibromatosis, Huntington's disease, depression, amyotrophic lateral sclerosis, multiple sclerosis); conditions that strike in adulthood (e.g. Creutzfeldt-Jakob disease, Lewy body disease, Parkinson's disease, Pick's disease); and other pathologies of the brain (e.g., brain mishaps, brain injury, coma, infections by various agents, dietary deficiencies, stroke, multi-infarct dementia, and cardiovascular accidents).

As used herein, by "therapy" is meant any treatment suitable for treating a disease. The purpose of the therapy is to reduce or eliminate the disease, or a symptom associated with the disease, or to inhibit the disease from progressing further. In addition, the term therapy may also include the close monitoring of an a symptomatic subject for the appearance of any symptoms of a disease. "Therapy for the treatment of a neurological disease" is any therapy suitable for treating a neurological disease. A suitable therapy can be a pharmacological agent or drug that may enhance cognitive function, motor function, or neuronal activity of the central nervous system, peripheral nervous system, or inhibit the further deterioration of any of these faculties. Drug efficacy of an appropriate drug can be determined by drug dosage, administration schedule, and prediction of therapeutic utility.

By "cholinomimetic therapy" is meant any drug that mimics the function of acetylcholine or enhances the activity of acetylcholine synthesizing cells. These drugs include, but are not limited to, inhibitors of acetylcholine degradation (acetylcholine esterase inhibitors such as tacrine), drugs that mimic acetylcholine structure and function, drugs that block acetylcholine uptake by neurons, and drugs that interact with pre-synaptic receptors to induce acetylcholine release from cholinergic neurons.

By "non-cholinomimetic therapy" is meant a therapy that, for example, utilizes a vasopressinergic modulator.

By "determining the presence of a variant PON1 allele" is meant subjecting a nucleic acid sample to any of a variety of detection techniques know in the art for elucidating a mutation in a nucleic acid (e.g., polymerase chain reaction (PCR), reverse transcriptase-PCR (RT-PCR), ligase-mediated chain reaction step, chip hybridization methods, sequencing nucleic acids by mass spectrometry, or restriction enzyme-mediated digestion). The mutation may be an insertion, deletion, or missense mutation. For example, in the presence of appropriately designed primers, a nucleic acid fragment can be amplified using PCR, and analyzed by restriction enzyme digestion that can reveal the presence of a variant allelic sequence. In addition, DNA sequencing may be employed using techniques known in the art. These nucleic acid techniques allow for a genotype determination of the PON1 locus.

Alternatively, phenotyping of the PON1 locus may be performed (and a genotype thus inferred) by using standard techniques for detecting the presence of a polypeptide having a particular amino acid change (e.g., antibodies, isoelectric focusing, and 2-D PAGE). For example, the presence of a variant paraoxonase polypeptide (e.g., Met54Leu) can be distinguished from a wild-type paraoxonase polypeptide using epitope-specific antibodies available in the art. Epitope-specific antibodies can be generated using the methods of Harlow and Lane (Antibodies. A Laboratory Manual. Cold Spring Harbor Laboratory, Cold Spring Harbor, N.Y. 1988). The sequence of the antigen used to generate antibodies capable of detecting variant PON1 alleles would include the mutated amino acid sites encoded by the variant alleles.

By "risk factor associated with a disease" is meant any risk factor for a disease known in the art. Examples of risk factors commonly associated with diseases include age, gender, diet, exercise, weight, the presence of another disease, and the occurrence of a specific genotype. Risk factors associated with a neurological disease in particular may include advanced age, lower intelligence, smaller head size, history of head trauma, mutations on chromosomes 1, 14, and 21, presence of an apoE4 allele, or the presence of a BCHE-K allele (see e.g., Cummings et al., *Neurology* (1 Supp.1):S2-S17, 1998).

By "subject at risk for a disease" is meant a subject identified or diagnosed as having a disease or having a genetic predisposition or risk for acquiring a disease using the methods of the invention and techniques available to those skilled in the art.

The present invention provides a number of advantages. For example, the methods described herein allow for the determination of a subject's PON1 genotype for the timely administration of an optimal treatment for the disease. The invention also allows for the identification of a subject at risk for a disease so that a prophylactic therapy for the treatment of the disease may be started before symptoms of the disease are apparent.

Other features and advantages of the invention will be apparent from the following detailed description and from the claims.

BRIEF DESCRIPTION OF THE DRAWINGS

FIG. 1 is a depiction of the cDNA sequence of the wild-type human paraoxonase 1 gene (PON1; SEQ ID NO: 1). The sequence encoding the first amino acid is underlined.

FIG. 2 is a depiction of the cDNA sequence of the human paraoxonase 1 allele (PON1) with the single nucleotide polymorphism at base 172 indicated in bold (SEQ ID NO: 2).

FIG. 3 is a depiction of the amino acid sequence encoded by the wild-type human paraoxonase 1 gene (PON1; SEQ ID NO: 3).

FIG. 4 is a depiction of the amino acid sequence encoded by the human paraoxonase 1 gene (PON1) with the single amino acid residue at position 54 substituted from a leucine (L) to a methionine (M), indicated in bold (SEQ ID NO: 4).

DETAILED DESCRIPTION OF THE INVENTION

Described herein are methods for diagnosing or treating a disease, as well as for identifying a subject for participation in a clinical trial, and for identifying a subject at risk for a disease. Techniques for carrying out the methods of the invention are now described in detail, using particular examples. These examples are provided for the purpose of illustrating the invention, and should not be construed as limiting.

EXAMPLE 1

Methods for Determining PON1 Allele Status PON1 Genotyping

The allele status of the PON1 gene in a large number of subjects diagnosed with Alzheimer's disease (N=136), and in age-matched healthy controls (N=70) was determined. Genotyping of each subject was performed by subjecting nucleic acid samples isolated from each subject, and encoding the PON1 gene, to a polymerase chain reaction (PCR) amplification step. The PCR amplification was conducted for 45 cycles using reaction conditions that involved a denaturation step at 94° C. for 25 seconds, a primer annealing step at 45° C. for 55 seconds, and a primer extension step at 72° C. for 45 seconds using the following oligonucleotides: 5'-AAT TTA GTT AAA GGA ATC GAA ACT GGC TCT GGA G-3' (SEQ ID NO: 5); and 5'-TTC ATT TTA TTT GAA AGT GGG CAT GGG TAT ACA GA-3' (SEQ ID NO: 6), in a total reaction volume of 50 $\mu$l.

Next, 10 $\mu$l of the PCR reaction product was digested with the restriction enzyme Hsp92II. The resulting product was analyzed using 3% NuSieve gel electrophoresis and visualized by ethidium bromide staining. The banding pattern of the Hsp92II-digested PCR product varied based on the genotype of the sample. A sample that was homozygous for methionine at amino acid position 54 produced 120-, 40-, and 25-base pair fragments. A sample which was heterozygous for methionine and leucine at amino acid position 54 produced 160-, 120-, 40-, and 25-base pair fragments. A sample which was homozygous for leucine at amino acid position 54 produced 160- and 25-base pair fragments.

The results of the genotyping were confirmed by performing DNA sequencing on a representative subset of the samples. The sequencing of the PON 1 polymorphism was conducted using an automated DNA sequencer according to the manufacturers instructions and using the following sequencing primer: 5'-TAA GTG AAA GCT TAA ACT GCC AGT C-3' (SEQ ID NO: 7).

PON1 Phenotyping

Phenotyping of the PON1 locus may be performed (and a genotype thus inferred) by using standard techniques for detecting the presence of a polypeptide having a particular amino acid change (e.g., antibodies, isoelectric focusing, and 2-D PAGE). For example, the presence of a variant paraoxonase polypeptide (e.g., Met54Leu) can be distinguished from a wild-type paraoxonase polypeptide using epitope-specific antibodies, as described in the art. Epitope-specific antibodies can be generated using the methods of Harlow and Lane (Antibodies. A Laboratory Manual. Cold Spring Harbor Laboratory, Cold Spring Harbor, N.Y. 1988). The sequence of the antigen used to generate antibodies capable of detecting variant PON1 alleles would include the variant amino acid sites encoded by the variant alleles.

Detection of PON1 DNA Sequence Polymorphisms Using Mass Spectrometry

The PON1 allele status can be determined by sequencing the allele using mass spectrometric techniques, for example, as described by Kamb (U.S. Pat. No. 5,869,242) or Köster (U.S. Pat. No. 5,547,835). In this method, the PON1 allelic region to be analyzed is amplified using PCR. The PON1 nucleic acid sample may be digested with a restriction enzyme to produce the fragment of interest (approximately 1 to 50 base pairs in length). If the polymorphism to be detected is a point mutation rather than an insertion or deletion mutation, the restriction enzymes chosen to produce the fragment should recognize the variant sequence, but not the wild-type sequence. The fragment is then denatured and analyzed by mass spectrometry, and the data obtained from the mass spectrometer is compared to the data obtained from the analysis of a wild-type control or other known polymorphisms. Differences between the spectra, either the appearance or disappearance of one or more peaks are an indication of a change in the amount of nucleic acid of a specific mass, and identifies the presence of a polymorphism.

In addition to the above-mentioned methods, the methods provided in any of the pending applications (Ser. No. 08/727,637,now U.S. Pat. No. 5,935,781; Ser. No. 08/766, 975, now U.S. Pat No. 6.022,683; Ser. Nos. 60/059,908; 08/991,850, now U.S. Pat. 6,251,587) and following references (Brindle N. et al., Hum. Mol. Genet. 7:933–935, 1998; Singleton et al., Hum. Mol. Genet. 7:937–939, 1998; Lehmann et al., Hum. Mol. Genet. 6:1933–1936, 1997; Richard et al., Lancet 349:539, 1997; and Gustincich S, et al., Biotechniques 11:298–300, 1998) may also be used, and are herein incorporated as references.

EXAMPLE 2

Use of a Variant PON1 Allele t Dignose a Patient as Having Alzheimer's

Disease and to Determine a Subject's Risk for Alzheimer's Disease

Table 1 shows the results of the PON1 allele status at amino acid position 54 of subjects diagnosed with Alzheimer's disease (AD) and age-matched controls. Compared to the control subjects, the percentage of subjects diagnosed with Alzheimer's disease, that were homozygous for methionine at amino acid position 54, was higher.

TABLE 1

Genotype of PON1 at Amino Acid Position 54

| subject | Met/Met (% of total) | Leu/Met (% of total) | Leu/Leu (% of total) |
|---|---|---|---|
| control | 4 (5.7) | 34 (48.6) | 32 (45.7) |
| AD | 22 (16.1) | 64 (47.1) | 50 (36.7) |

As shown in Table 2, there was a statistically significant increase in the frequency of the PON1 Met54 allele in the Alzheimer's disease cases versus the controls. This data suggests that the Met54 allele may be used as a marker in the diagnosis of Alzheimer's disease.

TABLE 2

Amino Acids Encoded by PON1 Alleles at Position 54

| amino acid | AD (% of total) | control (% of total) |
|---|---|---|
| Met | 108 (39.7) | 42 (30) |
| Leu | 164 (60.3) | 98 (70) |

Chi Square = 0.05
Odds Ratio = 1.54

When the PON1 allele status of the subjects diagnosed with Alzheimer's disease and the control subjects was sorted according to the Met/Met genotype versus other genotypes of PON1 at amino acid position 54, a Met54/Met54 homozygote was three times more likely to be in the AD group than in the control group. This data fuirther supports the use of the PON1 allele status as a marker in diagnosing a subject with Alzheimer's disease.

The determination of the PON1 allele status of a subject may also aid in the identification of an a symptomatic subject at risk for developing the disease in the future. It may be beneficial to determine the PON1 allele status of an a symptomatic subject so that a prophylactic therapy can be administered. It may be particularly helpful to determine the risk a subject has for a disease if the disease has a history of occurring in a family.

TABLE 3

Met/Met Genotype versus Other Genotypes of PON1 at Amino Acid Position 54

| genotype | AD | control |
|---|---|---|
| Met/Met | 22 | 4 |
| Leu/Met and Leu/Leu | 114 | 66 |

Chi Square = 0.032
Odds Ratio = 3.18

EXAMPLE 3

Identification of a Subject Sample for Use in a Clinical Trial of a Therapy for the Treatment of a Specific Disease The use of the PON1 allele status in diagnosing a subject with a disease may be important for determining and providing the optimal therapy to treat the disease. It is possible that a subject with a variant PON1 allele may respond differently to a therapy than a subject diagnosed with the same disease, but possessing a different PON1 allele status. This possibility can be tested in a clinical trial for a therapy for a disease, wherein the subjects are categorized based on their PON1 allele status, either before or after the actual clinical trial. For example, to demonstrate the effectiveness of the PON1 allele as a predictor of drug efficacy in subjects at risk for a neurological disease, the genomic DNA and cognitive scores of a patient group can be analyzed. The patients may be divided into two groups and one group is administered a therapy, while the other group is administered a placebo.

To quantify changes in cognitive function during the clinical trial, patients may be evaluated using the Mini Mental State Examination (MMSE). A baseline score is determined for each patient prior to treatment. Following a predetermined period of treatment time (e.g., 12 weeks of drug or placebo treatment), both patient groups are re-evaluated using the same test. The difference in MMSE score results, before and after treatment, is determined for each patient in the study with a positive change in score indicating an improvement in cognitive ability and a negative change in score indicating a deterioration.

PON1 genotyping is done as described in Example1 and each patient is categorized as either possessing at least one variant PON1 allele (e.g., Met54Leu) or lacking a variant allele. The predictive value of the variant PON1 allele on the response to the drug, as measured by a difference in MMSE score results, is used to determine its pharmacogenetic influence.

A clinical trial can be set up to test the efficacy of test compounds to treat any number of diseases for which a variant PON 1 allele has been determined to be associated with a subject diagnosed with a disease or at risk for developing the disease. For example, the clinical trial can be designed to analyze the efficacy of a test compound for the treatment of a neurological disease, including Alzheimer's disease, Parkinson's disease, and symptom complexes in Gulf War veterans. The clinical trial can also be designed to analyze test compounds in the treatment of other diseases such as cardiovascular disease and diabetic retinopathy in subjects with insulin-independent diabetes mellitus. The variant PON1 allele to be analyzed may vary based on the nature of the disease for which the clinical trial is designed. If subjects are genotyped after the completion of a clinical trial, the analyses may still be aimed a determining a relationship between a treatment for a disease and the allele to be assessed for efficacy.

Alternatively, if an a symptomatic subject has not yet been diagnosed with the disease but has been determined to be at risk, a similar clinical trial to the clinical trial described above may be carried out. Assessment of the efficacy of a drug chosen for the trial may include monitoring the subject over a period of time, and analyzing the delay of onset of the disease and the intensity of the disease at the time of onset, as well as measuring the onset of symptoms which are associated with the disease. A drug, that in a clinical trial eliminates or delays the onset of the disease, or reduces the symptoms of the disease may be a beneficial drug to use in patients that are determined to be at risk for developing a disease.

Test compounds which may be used in this invention include, but are not limited to, cholinomimetic (e.g., tacrine) or specific non-cholinomimetic (e.g., vasopressinergics) therapies, probucol, a monoamine oxidase inhibitor, muscarinic agonist, neurotrophic factor, noradrenergic factor, antioxidant, anti-inflammatory, corticotrophin-releasing hormone (CRH), somatostatin, substance P, neuropeptide Y, or thyrotrophin-releasing hormone (TRH), as well as drugs to treat cardiovascular diseases and diabetes and ramifications of these diseases.

Part of the clinical trial may include the optimization of drug administration, including dosage, timing of administration, toxicities or side effects, route of administration, and efficacy of the treatment.

EXAMPLE 4

Treating a Disease Based on a Subject's PON1 Allele Status

A test compound that has been shown to reduce or eliminate a disease, or to inhibit the disease from progressing further, can be used as a treatment for the disease or its associated symptoms. A subject diagnosed with a disease, or determined to be at risk for a disease, as determined by the PON1 allele status can be administered a therapy to treat the disease according to the subject's PON1 allele status. For example, a subject may be given one therapy if the subject is homozygous for a variant PON1 allele, and may be given a different therapy if the subject is heterozygous for the PON1 allele. As with the administration of a therapy in a clinical trial, the subject should be monitored to ensure that the correct dosage is administered, and that the side effects are minimal.

Other Embodiments of the Invention

Examples of the invention described herein provide methods for treating subjects with a neurological disease risk by determining the subject's PON1 allele status and providing a forecast of the subject's ability to respond to a given drug treatment. We conclude that the PON1 polymorphism is likely to have a similar predictive value for drugs acting through various pharmacological mechanisms. Thus, the methods of the invention may be used to determine a subject's response to drugs including, without limitation, cholinomimetic (e.g., tacrine) or specific non-cholinomimetic (e.g., vasopressinergics) therapies, probucol, a monoamine oxidase inhibitor, muscarinic agonist, neurotrophic factor, noradrenergic factor, antioxidant, anti-inflammatory, corticotrophin-releasing hormone (CRH), somatostatin, substance P, neuropeptide Y, or thyrotrophin-releasing hormone (TRH), as well as drugs to treat cardiovascular diseases and diabetes and ramifications of these diseases.

In addition, while determining the presence or absence of the PON1 allele Met54Leu may be a usefull diagnostic for a subject's disease or risk of developing a disease, other PON1 allelic variants of altered paraoxonase activity are envisioned as also being diagnostic or capable of risk assessment using the methods described herein. In particular, the methods of the invention may be used to diagnose, prognosticate, identify a subject for a clinical trial or a drug, or treat subjects with any PON1 mutations including the missense mutation GLU191ARG (which is equal to GLU192ARG using the alternate numbering method).

In addition, while the methods described herein are preferably used for the treatment of a human subject, non-human animals (e.g., pets and livestock) may also be treated using the methods of the invention.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

Other embodiments are within the claims.

What is claimed is:

1. A method for identiang a subject at risk for Alzheimer's disease, said method comprising determining the genotype of the PON1 gene of said subject at the nucleotides encoding amino acid position 54, wherein detection of methionine homozygosity at position 54 indicates an increased risk for Altheimer's disease.

2. A method for stratifying a subject in a subgroup of a clinical trial of a therapy for the treatment of Alzheimer's disease, said method comprising determining the genotype of the PON1 gene of said subject at the nucleotides encoding amino acid position 54, wherein said subject is stratified into a subgroup for said clinical trial of said therapy based upon the amino acid position 54 of the PON1 gene.

3. The method of claim 2, wherein said therapy is a cholinomimetic therapy.

4. The method of claim 3, wherein said cholinomimetic therapy is tacrine.

5. The method of claim 2, wherein said therapy is a non-cholinomimetic therapy.

6. The method of claim 5, wherein said non-cholinomimetic therapy is a vasopressinergic therapy.

7. The method of claim 2, wherein said therapy is selected from the group consisting of probucol, a monoamine oxidase inhibitor, a muscarinic agonist, a neurotrophic factor, a noradrenergic factor, an antioxidant, an anti-inflammatory, corticotrophin-releasing hormone (CRH), somatostatin, substance P, neuropeptide Y, and thyrotrophin-releasing hormone (TRH).

* * * * *

SEQUENCE LISTING

<160> NUMBER OF SEQ ID NOS: 7

<210> SEQ ID NO 1
<211> LENGTH: 1346
<212> TYPE: DNA
<213> ORGANISM: Homo sapiens

<400> SEQUENCE: 1

```
cccccgacca tggcgaagct gattgcgctc accctcttgg ggatgggact ggcactcttc      60

aggaaccacc agtcttctta ccaaacacga cttaatgctc tccgagaggt acaacccgta     120

gaacttccta actgtaattt agttaaagga atcgaaactg gctctgaaga cttggagata     180

ctgcctaatg gactggcttt cattagctct ggattaaagt atcctggaat aaagagcttc     240

aaccccaaca gtcctggaaa aatacttctg atggacctga atgaagaaga tccaacagtg     300

ttggaattgg ggatcactgg aagtaaattt gatgtatctt catttaaccc tcatgggatt     360

agcacattca cagatgaaga taatgccatg tacctcctgg tggtgaacca tccagatgcc     420

aagtccacag tggagttgtt taaatttcaa gaagaagaaa aatcgctttt gcatctaaaa     480

accatcagac ataaacttct gcctaatttg aatgatattg ttgctgtggg acctgagcac     540

ttttatggca caaatgatca ctattttctt gacccctact tacaatcctg ggagatgtat     600

ttgggtttag cgtggtcgta tgttgtctac tatagtccaa gtgaagttcg agtggtggca     660

gaaggatttg attttgctaa tggaatcaac atttcacccg atggcaagta tgtctatata     720

gctgagttgc tggctcataa gattcatgtg tatgaaaagc atgctaattg gactttaact     780

ccattgaagt cccttgactt taataccctc gtggataaca tatctgtgga tcctgagaca     840

ggagaccttt gggttggatg ccatcccaat ggcatgaaaa tcttcttcta tgactcagag     900

aatcctcctg catcagaggt gcttcgaatc cagaacattc taacagaaga acctaaagtg     960

acacaggttt atgcagaaaa tggcacagtg ttgcaaggca gtacagttgc ctctgtgtac    1020

aaagggaaac tgctgattgg cacagtgttt cacaaagctc tttactgtga gctctaacag    1080

accgatttgc acccatgcca tagaaactga ggccattatt tcaaccgctt gccatattcc    1140

gaggacccag tgttcttagc tgaacaatga atgctgaccc taaatgtgga catcatgaag    1200

catcaaagca ctgtttaact gggagtgata tgatgtgtag ggcttttttt tgagaataca    1260

ctatcaaatc agtcttggaa tacttgaaaa cctcatttac cataaaaatc cttctcacta    1320

aaatggataa atcagttaaa aaaaaa                                        1346
```

<210> SEQ ID NO 2
<211> LENGTH: 1346
<212> TYPE: DNA
<213> ORGANISM: Homo sapiens

<400> SEQUENCE: 2

```
cccccgacca tggcgaagct gattgcgctc accctcttgg ggatgggact ggcactcttc      60

aggaaccacc agtcttctta ccaaacacga cttaatgctc tccgagaggt acaacccgta     120

gaacttccta actgtaattt agttaaagga atcgaaactg gctctgaaga catggagata     180

ctgcctaatg gactggcttt cattagctct ggattaaagt atcctggaat aaagagcttc     240

aaccccaaca gtcctggaaa aatacttctg atggacctga atgaagaaga tccaacagtg     300

ttggaattgg ggatcactgg aagtaaattt gatgtatctt catttaaccc tcatgggatt     360

agcacattca cagatgaaga taatgccatg tacctcctgg tggtgaacca tccagatgcc     420
```

-continued

```
aagtccacag tggagttgtt taaatttcaa gaagaagaaa aatcgctttt gcatctaaaa    480

accatcagac ataaacttct gcctaatttg aatgatattg ttgctgtggg acctgagcac    540

ttttatggca caaatgatca ctattttctt gacccctact tacaatcctg ggagatgtat    600

ttgggtttag cgtggtcgta tgttgtctac tatagtccaa gtgaagttcg agtggtggca    660

gaaggatttg attttgctaa tggaatcaac atttcacccg atggcaagta tgtctatata    720

gctgagttgc tggctcataa gattcatgtg tatgaaaagc atgctaattg gactttaact    780

ccattgaagt cccttgactt taataccctc gtggataaca tatctgtgga tcctgagaca    840

ggagaccttt gggttggatg ccatcccaat ggcatgaaaa tcttcttcta tgactcagag    900

aatcctcctg catcagaggt gcttcgaatc cagaacattc taacagaaga acctaaagtg    960

acacaggttt atgcagaaaa tggcacagtg ttgcaaggca gtacagttgc ctctgtgtac   1020

aaagggaaac tgctgattgg cacagtgttt cacaaagctc tttactgtga gctctaacag   1080

accgatttgc acccatgcca tagaaactga ggccattatt tcaaccgctt gccatattcc   1140

gaggacccag tgttcttagc tgaacaatga atgctgaccc taaatgtgga catcatgaag   1200

catcaaagca ctgtttaact gggagtgata tgatgtgtag ggcttttttt tgagaataca   1260

ctatcaaatc agtcttggaa tacttgaaaa cctcatttac cataaaaatc cttctcacta   1320

aaatggataa atcagttaaa aaaaaa                                        1346
```

<210> SEQ ID NO 3
<211> LENGTH: 355
<212> TYPE: PRT
<213> ORGANISM: Homo sapiens

<400> SEQUENCE: 3

```
Met Ala Lys Leu Ile Ala Leu Thr Leu Leu Gly Met Gly Leu Ala Leu
 1               5                  10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Thr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205
```

-continued

```
Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355


<210> SEQ ID NO 4
<211> LENGTH: 355
<212> TYPE: PRT
<213> ORGANISM: Homo sapiens

<400> SEQUENCE: 4

Met Ala Lys Leu Ile Ala Leu Thr Leu Leu Gly Met Gly Leu Ala Leu
 1               5                  10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Met Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Thr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
```

-continued

```
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355


<210> SEQ ID NO 5
<211> LENGTH: 34
<212> TYPE: DNA
<213> ORGANISM: Artificial Sequence
<220> FEATURE:
<223> OTHER INFORMATION: Oligonucleotide derived from Homo sapiens
      sequence

<400> SEQUENCE: 5

attttagtta aaggaatcga aactggctct ggag                              34


<210> SEQ ID NO 6
<211> LENGTH: 35
<212> TYPE: DNA
<213> ORGANISM: Artificial Sequence
<220> FEATURE:
<223> OTHER INFORMATION: Oligonucleotide derived from Homo sapiens
      sequence

<400> SEQUENCE: 6

ttcattttat ttgaaagtgg gcatgggtat acaga                             35


<210> SEQ ID NO 7
<211> LENGTH: 25
<212> TYPE: DNA
<213> ORGANISM: Artificial Sequence
<220> FEATURE:
<223> OTHER INFORMATION: Oligonucleotide derived from Homo sapiens
      sequence

<400> SEQUENCE: 7

taagtgaaag cttaaactgc cagtc                                        25
```